United States Patent
Hsu et al.

(10) Patent No.: US 12,240,858 B2
(45) Date of Patent: Mar. 4, 2025

(54) CRYSTALLINE FORMS OF (S, E)-4-(DIMETHYLAMINO)-N-(3-(4-(2-HYDROXY-1-PHENYLETHYLAMINO)-6-PHENYLFURO[2,3-D]PYRIMIDIN-5-YL) PHENYL)BUT-2- ENAMIDE FREE BASE

(71) Applicant: Chuan Shih, Taipei (TW)

(72) Inventors: Tsu-An Hsu, Taipei (TW); Hsing-Pang Hsieh, Taipei (TW); Sue-Ming Chang, Taipei (TW)

(73) Assignee: ANBOGEN THERAPEUTICS, INC, Taipei (TW)

( * ) Notice: Subject to any disclaimer, the term of this patent is extended or adjusted under 35 U.S.C. 154(b) by 341 days.

(21) Appl. No.: 17/858,321

(22) Filed: Jul. 6, 2022

(65) Prior Publication Data
US 2023/0021909 A1    Jan. 26, 2023

Related U.S. Application Data

(60) Provisional application No. 63/218,504, filed on Jul. 6, 2021.

(51) Int. Cl.
*C07D 491/048*    (2006.01)

(52) U.S. Cl.
CPC ...... *C07D 491/048* (2013.01); *C07B 2200/13* (2013.01)

(58) Field of Classification Search
CPC ............ C07B 2200/13; C07D 491/048; C07D 491/04; A61K 31/519; A61P 35/00
See application file for complete search history.

(56) References Cited

U.S. PATENT DOCUMENTS
2010/0120805 A1    5/2010    Hsieh et al.

FOREIGN PATENT DOCUMENTS
WO    WO2011/099764 A2    8/2011

OTHER PUBLICATIONS

First office action and search report of the corresponding Singapore patent application No. 11202308218Y dated Feb. 9, 2024.
National Center for Biotechnology Information. "PubChem Compound Summary for CID 155565961" *PubChem*, https://pubchem.ncbi nlm.nih.gov/compound/155565961, created Feb. 17, 2021.

*Primary Examiner* — Kortney L. Klinkel
*Assistant Examiner* — Padmaja S Rao
(74) *Attorney, Agent, or Firm* — Muncy, Geissler, Olds & Lowe, P.C.

(57) ABSTRACT

Disclosed herein is a specific crystalline forms of (S, E)-4-(dimethylamino)-N-(3-(4-(2-hydroxy-1-phenylethylamino)-6-phenylfuro[2,3-d]pyrimidin-5-yl)phenyl)but-2-enamide (ABT-101) free base, the pharmaceutical composition and capsule comprising the same, and the medical application thereof. Said crystalline forms of ABT-101 free base can exhibit unexpected stability and improved pharmacokinetic properties compared to other forms or salt thereof, thereby allowing said compound more suitable for drug development and satisfying the requirements for bioavailability and drug efficacy.

18 Claims, 6 Drawing Sheets

CRYSTALLINE FORMS OF (S, E)-4-(DIMETHYLAMINO)-N-(3-(4-(2-HYDROXY-1-PHENYLETHYLAMINO)-6-PHENYLFURO [2,3-D]PYRIMIDIN-5-YL)PHENYL)BUT-2-ENAMIDE FREE BASE

CROSS REFERENCE

This application claims priority to, and the benefit of, U.S. Provisional Application No. 63/218,504, filed on Jul. 6, 2021, the content thereof is incorporated by reference herein.

FIELD OF THE INVENTION

The present invention relates to new crystalline forms of (S,E)-4-(dimethylamino)-N-(3-(4-(2-hydroxy-1-phenylethylamino)-6-phenylfuro[2,3-d]pyrimidin-5-yl)phenyl)but-2-enamide (ABT-101) free base, to pharmaceutical compositions and capsules comprising the same, and to methods of using the crystalline forms in the treatment of cancer.

BACKGROUND OF THE INVENTION

Epidermal growth factor receptor (EGFR) is a subfamily of four closely related receptor tyrosine kinases: EGFR, HER2, HER3, and HER4. Binding of EGF ligand to the extracellular domain of EGFR leads to activation of the intracellular protein-tyrosine kinase activity. As a result, autophosphorylation of several tyrosine residues in the C-terminal domain of EGFR occurs. (Kamath, S. Buolamwini, J. K., *Med. Res. Rev.* 2006, 26, 569-594).

For patients suffering from cancers, targeted therapies against EFGR and HER2 are standard treatment regimens today. More specifically, several EGFR kinase inhibitors, such as Gefitinib and Erlotinib, have been used for treating Non-Small Cell Lung cancer (NSCLC). However, only 10-20% of the NSCLC patients respond to Gefitinib treatment, mainly due to drug resistance caused by T790M mutation in EGFR kinase. Besides, HER2 exon 20 insertions are also common mutations found in 1-3% of NSCLC patients (*J. Med. Chem.* 2019, 62, 10108-10123). While there is currently no EGFR- or HER2-directed therapies are approved to be specific treatment to said mutations, thus, it is of great interest to develop EGFR kinase inhibitors, especially those which can inhibit activity of EGFR mutants (e.g., the T790M mutant) and HER2 exon 20 insertions, as anti-cancer drugs.

Accordingly, several fused bicyclic or tricyclic compounds including ABT-101 that can be used to inhibit activity of EGFR are disclosed in U.S. Pat. No. 8,507,502B2, which are herein incorporated by reference in its entirety. Nevertheless, the differences in various aspects between crystalline forms of said compounds have barely been discussed.

SUMMARY OF THE INVENTION

The invention is based on the discovery that certain crystalline forms of (S, E)-4-(dimethylamino)-N-(3-(4-(2-hydroxy-1-phenylethylamino)-6-phenylfuro[2,3-d]pyrimidin-5-yl)phenyl)but-2-enamide (ABT-101) free base, which exhibit unexpected stability and improved pharmacokinetic properties.

Accordingly, the present invention provides a crystalline form of (S, E)-4-(dimethylamino)-N-(3-(4-(2-hydroxy-1-phenylethylamino)-6-phenylfuro[2,3-d]pyrimidin-5-yl)phenyl)but-2-enamide (ABT-101) free base characterized by an X-ray powder diffraction pattern comprising peaks at 2θ values of 4.8°±0.2°, 9.5°+0.2°, 10.2°±0.2°, 12.5°±0.2°, 15.0°±0.2°, 18.4°±0.2° and 20.8°±0.2°.

Further, the crystalline form provided herein is characterized by an X-ray powder diffraction pattern further comprising a peak at 2θ value of 8.7°±0.2°.

Further, the crystalline form provided herein is characterized by an X-ray powder diffraction pattern further comprising a peak at 2θ value of 19.4°±0.2°.

Further, the crystalline form provided herein is characterized by an X-ray powder diffraction pattern further comprising a peak at 2θ value of 23.1°+0.2°.

Further, the crystalline form provided herein has a melting point temperature of 170 to 195° C.

Further, the crystalline form provided herein has an enthalpy of melting of 75 to 85° C.

The present invention provides a pharmaceutical composition comprising the crystalline form provided herein and a pharmaceutically acceptable carrier or excipient.

In another aspect, the present invention provides a capsule comprising the pharmaceutical composition provided herein.

Further, the capsule provided herein comprises from 0.1 to 200 mg of said crystalline form.

Further, the capsule provided herein comprises from 25 to 100 mg of said crystalline form.

Further, the capsule provided herein comprises from 50 to 100 mg of said crystalline form.

The present invention provides a method of treating cancer, comprising administering to a patient in need thereof a therapeutically effective amount of the crystalline form provided herein.

Further, the crystalline form provided herein is a EGFR inhibitor, a HER2 inhibitor or a tumor-agnostic inhibitor.

Further, according to the method of the present invention, wherein the cancer is peritoneal cancer, small intestine cancer, non-small cell lung cancer (NSCLC), neuroendocrine cancer, salivary gland, bladder cancer, breast cancer, cervix cancer, bile duct cancer, esophageal cancer, stomach cancer, early gastric cancer, colorectal cancer, prostate cancer, ovarian cancer, head and neck cancer, endometrial cancer, kidney cancer, melanoma cancer, sarcoma cancer, pancreatic cancer, small cell lung cancer (SCLC), leukemia cancer, brain cancer or thyroid cancer.

Accordingly, the effect of the present invention is that the specific crystalline form of ABT-101 free base can exhibit unexpected stability and improved pharmacokinetic properties compared to other forms or salt thereof, thereby allowing said compound more suitable for drug development and satisfying the requirements for bioavailability and drug efficacy.

BRIEF DESCRIPTION OF THE DRAWINGS

In order to make the above and other objects, features, advantages and embodiments of the present invention more obvious and understandable, the drawings are described as follows.

DETAILED DESCRIPTION OF THE INVENTION

Definition

The terms used in this specification are generally within the scope of the present invention and the specific context of each term has its usual meaning in related fields. The specific terms used to describe the present invention in this specification will be described below or elsewhere in this specification, so as to help people in the industry understand the relevant description of the present invention. The same term has the same scope and meaning in the same context. In addition, there is more than one way to express the same thing; therefore, the terms discussed in this article may be replaced by alternative terms and synonyms, and whether a term is specified or discussed in this article does not have any special meaning. This article provides synonyms for certain terms, but the use of one or more synonyms does not mean that other synonyms are excluded.

As used herein, unless the context clearly indicates otherwise, "a" and "the" can also be interpreted as plural. In addition, in this specification and the scope of the attached patent application, unless otherwise stated in the context, "middle" and "inner" include "located in"; and unless otherwise stated in the context, the direction of the tip of the projectile was defined as "upper" or "lower". Furthermore, titles and subtitles may be attached to the description for easy reading, but these titles do not affect the scope of the present invention.

As used herein, the term "crystalline" may refer to having a regularly repeating arrangement of molecules or external face planes. Crystalline forms may differ with respect to thermodynamic stability, physical parameters, X-ray structure and preparation processes.

As used herein, the term "amorphous" may refer to a form of a compound, or a salt or molecular complex of a compound, that lacks long range crystalline order where the x-ray diffraction pattern lacks Bragg reflections.

As used herein, the term "solid form" may refer to a crystalline solid form or phase, including crystalline free base, crystalline salt, or a cocrystal, as well as an amorphous phase, including an amorphous dispersion.

As used herein, unless otherwise indicated, the term "treating" means reversing, alleviating, inhibiting the progress of, or preventing the disorder or condition to which such term applies, or one or more symptoms of such disorder or condition. The term "treatment", unless otherwise indicated, refers to the act of treating as "treating as defined immediately above.

As used herein, the term "effective amount" or "therapeutically effective amount" refers to that amount of a compound or combination of compounds that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimens to be followed, whether the compound is administered in combination with other compounds, timing of administration, the tissue to which it is administered, and the physical delivery system in which the compound is carried.

In an embodiment, the present invention provides a crystalline form of (S, E)-4-(dimethylamino)-N-(3-(4-(2-hydroxy-1-phenylethylamino)-6-phenylfuro[2,3-d]pyrimidin-5-yl)phenyl)but-2-enamide (ABT-101, represented by Formula I) free base.

(Formula I)

Said crystalline form is characterized by an X-ray powder diffraction pattern comprising peaks at 2θ values of 4.8°±0.2°, 9.5°±0.2°, 10.2°±0.2°, 12.5°±0.2°, 15.0°+10.2°, 18.4°±0.2° and 20.8°±0.2°.

Preferably, the crystalline form provided herein is characterized by an X-ray powder diffraction pattern further comprising a peaks at 2θ value of 8.7°±0.2°.

Preferably, the crystalline form provided herein is characterized by an X-ray powder diffraction pattern further comprising a peaks at 2θ value of 19.4°±0.2°.

Preferably, the crystalline form provided herein is characterized by an X-ray powder diffraction pattern further comprising a peaks at 2θ value of 23.1°±0.2°.

In another embodiment, said crystalline form is characterized by an X-ray powder diffraction pattern comprising peaks selected from the group consisting of 4.8°±0.2°, 8.70±0.20, 9.5°±0.2°, 10.2°±0.2°, 12.5°±0.2°, 15.0°±0.2°, 18.4°+0.2°, 19.4°±0.2°, 20.8°±0.2° and 23.1°±0.2°, with peak positions measured in 2.

It is known in the art that an X-ray powder diffraction (XPRD) pattern may be obtained which has one or more measurement errors depending on measurement conditions (such as equipment, sample preparation or instrument used). In particular, it is generally known that intensities in an X-ray powder diffraction pattern may vary depending on measurement conditions and sample preparation. For example, persons skilled in the art of X-ray powder diffraction will realize that the relative intensities of peaks may vary according to the orientation of the sample under test and based on the type and settings of the instrument used. The skilled person will also realize that the position of reflections can be affected by the precise height at which the sample sits in the diffractometer, the sample's surface planarity, and the zero calibration of the diffractometer. Hence a person skilled in the art will appreciate that the diffraction pattern data presented herein is not to be construed as absolute and any crystalline form that provides a power diffraction pattern substantially the same as those disclosed herein fall within the scope of the present disclosure. For further information, see Jenkins and Snyder, *Introduction to X-Ray Powder Diffractotmetry*, John Wiley & Sons, 1996.

In an embodiment, the crystalline form provided herein has a melting point temperature of 170 to 195° C.; more particularly, said melting point temperature is, for example, 170, 171, 172, 173, 174, 175, 176, 177, 178, 179, 180, 181, 182, 183, 184, 185, 186, 187, 188, 189, 190, 191, 192, 193, 194 or 195° C. In an embodiment, the crystalline form provided herein has an enthalpy of melting of 75 to 85° C.; more particularly, said enthalpy of melting is, for example, 75, 76, 77, 78, 79, 80, 81, 82, 83, 84 or 85° C. In each if the foregoing embodiment, the melting point temperature and enthalpy of melting characterizing the crystalline form of the present invention are analyzed by differential scanning calorimetry (DSC), including modulated differential scanning calorimetry or temperature-modulated differential scanning calorimetry.

In an embodiment, the present invention provides a pharmaceutical composition comprising the crystalline form provided herein and a pharmaceutically acceptable carrier or excipient. More specifically, said pharmaceutical composition is a EGFR inhibitor, a HER2 inhibitor or a tumor-agnostic inhibitor. Where desired, the pharmaceutical compositions contain a pharmaceutically acceptable salt thereof, and one or more pharmaceutically acceptable excipients, carriers, including inert solid diluents and fillers, diluents, permeation enhancers, solubilizers, or adjuvants. In some embodiments, the concentration of the crystalline form of ABT-101 free base provided in the pharmaceutical compositions of the invention is independently less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, or 0.001%, w/w, w/v, or v/v, relative to the total mass or volume of the pharmaceutical composition. In some embodiments, the concentration of the crystalline form of ABT-101 free base provided in the pharmaceutical compositions of the invention is independently greater than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, or 0.001%, w/w, w/v, or v/v, relative to the total mass or volume of the pharmaceutical composition.

Examples of suitable fillers for use in the pharmaceutical composition disclosed herein include, but are not limited to, lactose monohydrate, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Examples of lubricants for use in the pharmaceutical composition disclosed herein include, but are not limited to, calcium stearate, magnesium stearate, mineral oil, light mineral oil, glycerin, sorbitol, mannitol, polyethylene glycol, other glycols, stearic acid, sodium stearyl fumarate, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a silica gel, a coagulated aerosol of synthetic silica, silicified microcrystalline cellulose, or mixtures thereof.

Examples of disintegrants that can be used in the pharmaceutical composition disclosed herein include, but are not limited to, croscarmellose sodium, alginic acid, calcium carbonate, microcrystalline cellulose, crospovidone, polacrilin potassium, sodium starch glycolate, potato or tapioca starch, other starches, pre-gelatinized starch, other starches, clays, other algins, other celluloses, gums or mixtures thereof In another aspect, the present invention provides a capsule comprising said pharmaceutical composition. Further, the capsule provided herein comprises from 0.1 to 200 mg of the crystalline form of ABT-101 free base; more particularly, the amount of said crystalline form is, for example, 0.1, 0.2, 0.3, 0.4, 0.5, 0.6, 0.7, 0.8, 0.9, 1, 5, 10, 20, 30, 40, 50, 60, 70, 80, 90, 100, 110, 120, 130, 140, 150, 160, 170, 180, 190 or 200 mg. Preferably, the capsule provided herein comprises from 25 to 100 mg of the crystalline form of ABT-101 free base; more particularly, the amount of said crystalline form is, for example, 25, 30, 35, 40, 45, 50, 55, 60, 65, 70, 75, 80, 85, 90, 95, 100 mg. More preferably, the capsule provided herein comprises from 50 to 100 mg of the crystalline form of ABT-101 free base; more particularly, the amount of said crystalline form is, for example, 50, 55, 60, 65, 70, 75, 80, 85, 90, 95, 100 mg.

Pharmaceutical compositions of the invention suitable for oral administration can be presented as discrete dosage forms, such as capsules, sachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil emulsion. Pharmaceutical compositions of the invention also include powder for reconstitution, powders for oral consumptions, bottles (such as powder or liquid in bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation.

The present invention provides a method of treating cancer, comprising administering to a patient in need thereof a therapeutically effective amount of the crystalline form of ABT-101 free base.

In some embodiments, the crystalline form of ABT-101 free base administered is a EGFR inhibitor, a HER2 inhibitor or a tumor-agnostic inhibitor.

In selected embodiments, the crystalline form of ABT-101 free base is administered in a single dose. A single dose of the crystalline form of ABT-101 free base may also be used for treatment of an acute condition. In selected embodiments, the crystalline form of ABT-101 free base is administered in multiple doses. Dosing may be about once, twice, three times, four times, five times, six times, or more than six times per day. Dosing may be about once a month, once every two weeks, once a week, or once every other day. In other embodiments, the crystalline form of ABT-101 free base is administered about once per day to about 6 times per day. In another embodiment the administration of the crystalline form of ABT-101 free base, continues for less than about 7 days. In yet another embodiment the administration continues for more than about 6, 10, 14, 28 days, two months, six months, or one year. In some cases, continuous dosing is achieved and maintained as long as necessary.

Administration of the active pharmaceutical ingredients of the invention may continue as long as necessary. In selected embodiments, the crystalline form of ABT-101 free base, are administered for more than 1, 2, 3, 4, 5, 6, 7, 14, or 28 days. In some embodiments, the crystalline form of ABT-101 free base are administered for less than 28, 14, 7, 6, 5, 4, 3, 2, or 1 day. In selected embodiments, the crystalline form of ABT-101 free base is administered chronically on an ongoing basis, e.g., for the treatment of chronic effects. In some embodiments, an effective dosage of the crystalline form of ABT-101 free base is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of the crystalline form of ABT-101 free base is about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In some embodiments, an effective dosage of the crystalline form of ABT-101 free base is 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg.

Further, according to the method of the present invention, wherein the cancer is peritoneal cancer, small intestine cancer, non-small cell lung cancer (NSCLC), neuroendocrine cancer, salivary gland, bladder cancer, breast cancer, cervix cancer, bile duct cancer, esophageal cancer, stomach cancer, early gastric cancer, colorectal cancer, prostate cancer, ovarian cancer, head and neck cancer, endometrial cancer, kidney cancer, melanoma cancer, sarcoma cancer, pancreatic cancer, small cell lung cancer (SCLC), leukemia cancer, brain cancer or thyroid cancer.

Although the numerical ranges and parameters used to define the present invention are approximate values, the relevant values in the specific embodiments have been presented as accurately as possible. However, any numerical value inevitably contains standard deviations due to individual test methods. Here, "about" generally means that the actual value is within plus or minus 10%, 5%, 1%, or 0.5% of a specific value or range. Or, the term "about" means that the actual value falls within the acceptable standard error of the average value, which is determined by those with ordinary knowledge in the field to which the present invention belongs. Therefore, unless otherwise stated to the contrary, the numerical parameters disclosed in this specification and the accompanying patent application are approximate values and can be changed as required. At least these numerical parameters should be understood as the indicated significant digits and the values obtained by applying the general rounding method.

EXAMPLES

In this section, the contents of the present invention will be described in detail through the following examples. These examples are for illustration only, and those skilled in the art can easily think of various modifications and changes. As such, various embodiments of the present invention will be described in detail below, while the invention is not limited to said various embodiments listed in this specification Methods and Material X-ray Powder Diffraction (XPRD): XPRD data shown as follows is collected according to the following measurement parameters:
Instrument: X-ray Diffractometer D2 Phaser, Bruker;
Anode: Cu;
Generator voltage: 30 kV;
Generator current: 10 mA;
Scan type: Coupled Two Theta/Theta;
Divergence silt: 0.2 mm;
Anti-scanning screen: 0.5 mm;
Start angle: 3.5 deg;
End angle: 40 deg;
Step size: 0.03 deg/step;
Time: 1.0 sec/step;
Differential Scanning Calorimetery (DSC): DSC measurements in the present invention are carried out using a TA Q20, Thermal Analysis Instruments. Sample weight of 3.0-15.0 mg was placed in a hermetically sealed aluminum pan. The sample was equilibrated to 100° C. and then ramped to 200° C. at a scan rate of 5° C./min. Dry nitrogen was used as the purge gas.

Example 1

Preparation of crystalline forms of ABT-101 free base
ABT-101 compound is obtained through the process as follows:
A mixture of S-2-[5-(3-Nitro-phenyl)-6-phenyl-furo[2,3-d]pyrimidin-4-ylamino]-2-phenyl-ethanol (1 g, 0.002 mmol) and 5% Pd/C (10 mg) in MeOH (10 mL) was hydrogenated at 3 atmospheric pressure for 8 h. Filtered the reaction mixture over celite, removed solvents under vacuum to give S-2-[5-(3-amino-phenyl)-6-phenyl-furo[2,3-d]pyrimidin-4-ylamino]-2-phenyl-ethanol. To a mixture of the above compound in DCM (5 mL), was added 4-bromocrotonoic acid (422 mg, 2.55 mmol), EDCI (490 mg, 2.55 mmol) and stirred the reaction mixture for 8 h. Then added N,N-dimethylamine (1.18 ml, 23.2 mmol) and continued stirring for 8 h at room temperature. Added water to the reaction mixture and extracted with dichloromethane (3×20 mL). Combined organics dried over MgSO4, concentrated under vacuum and the residue purified over silica gel flash column chromatography using dichloromethane:methanol (20:1) to give the ABT-101 compound. The fallowing purification was executed by re-crystallization with hot Acetone at 53~58° C. After the mixture was cooled to 0~5° C. to yield ABT-101 crystals, solvent was then centrifuged followed by washing of ABT-101 crystals with Acetone to generate ABT-101.

Figure 1:
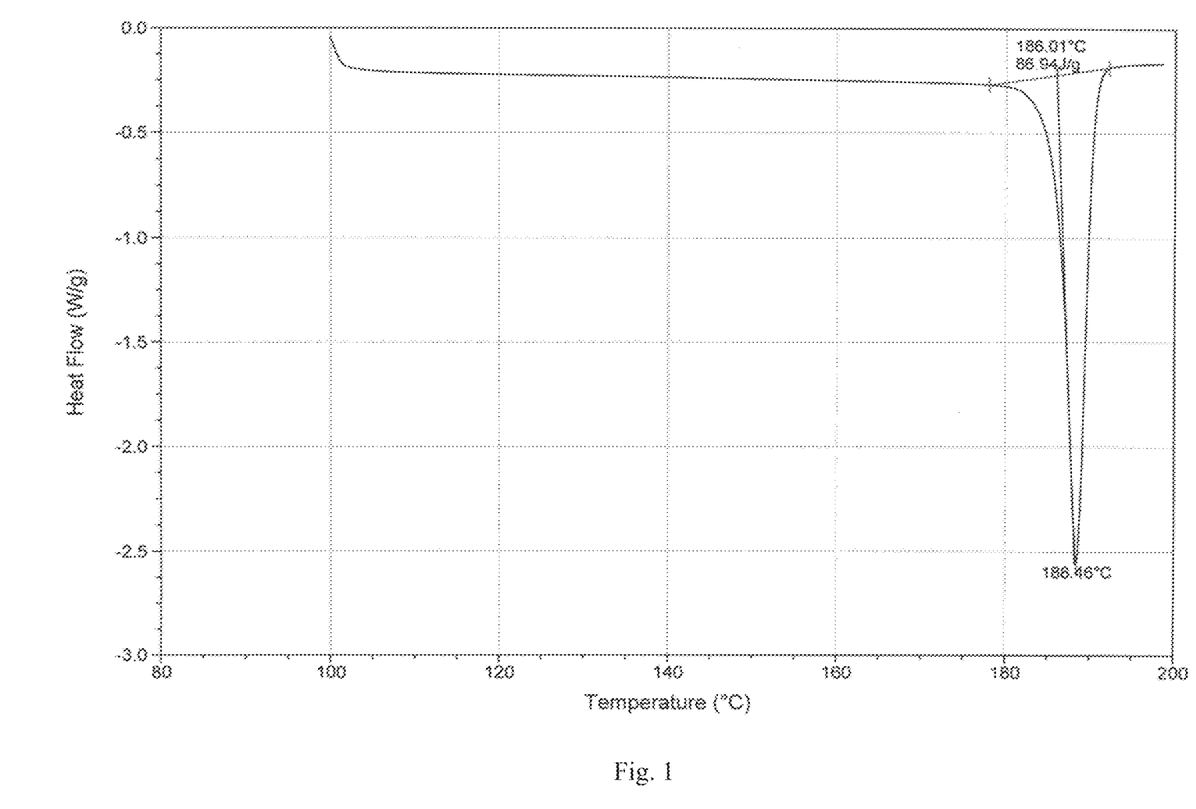
FIG. 1 illustrates a DSC curve for crystalline of ABT-101 free base.

Further, the ABT-101 compound obtained is crystallized using different solvents. The corresponding samples and the descriptions thereof are described in Table 1. Besides, a DSC curve for crystalline of ABT-101 free base is shown in FIG. 1.

TABLE 1

| ABT-101 | Solvent used for crystallization | Solute/solvent | Yield (%) | Melting point (° C) | HPLC purity (%) |
|---|---|---|---|---|---|
| 1 | Acetonitrile | 3 g/60 mL | 80 | 185~186 | 96.3 |
| 2 | Acetone | 500 mg/2 mL | 61 | 177~180 | 99.5 |
| 3 | Acetone | 500 mg/4 mL | 57 | 182~185 | 99.7 |
| 4 | Ethanol | 500 mg/3 mL | 47 | 182~185 | 99.1 |
| 5 | Isopropanol | 500 mg/3 mL | 66 | 180~184 | 98.8 |
| 6 | Ethyl acetate | 500 mg/4 mL | 78 | 181~185 | 99.3 |
| 7 | 6 mL toluene and 1 mL THF | 500 mg/ (6 + 1) mL | 72 | 179~182 | 98.8 |
| 8 | 2 mLTHF and 1 mL acetonitrile | 500 mg/ (2 + 1) mL | 45 | 188~190 | 100 |
| 9 | 1 mL THF and 2 mL acetonitrile | 500 mg/ (1 + 2) mL | 68 | 185~188 | 99.8 |
| 10 | Acetonitrile | 14 g/ 300 mL | 83 | 183~186 | 99.8 |

Example 2

Physical Characterization of Crystalline Forms of ABT-101 Free Base

Figure 2A:
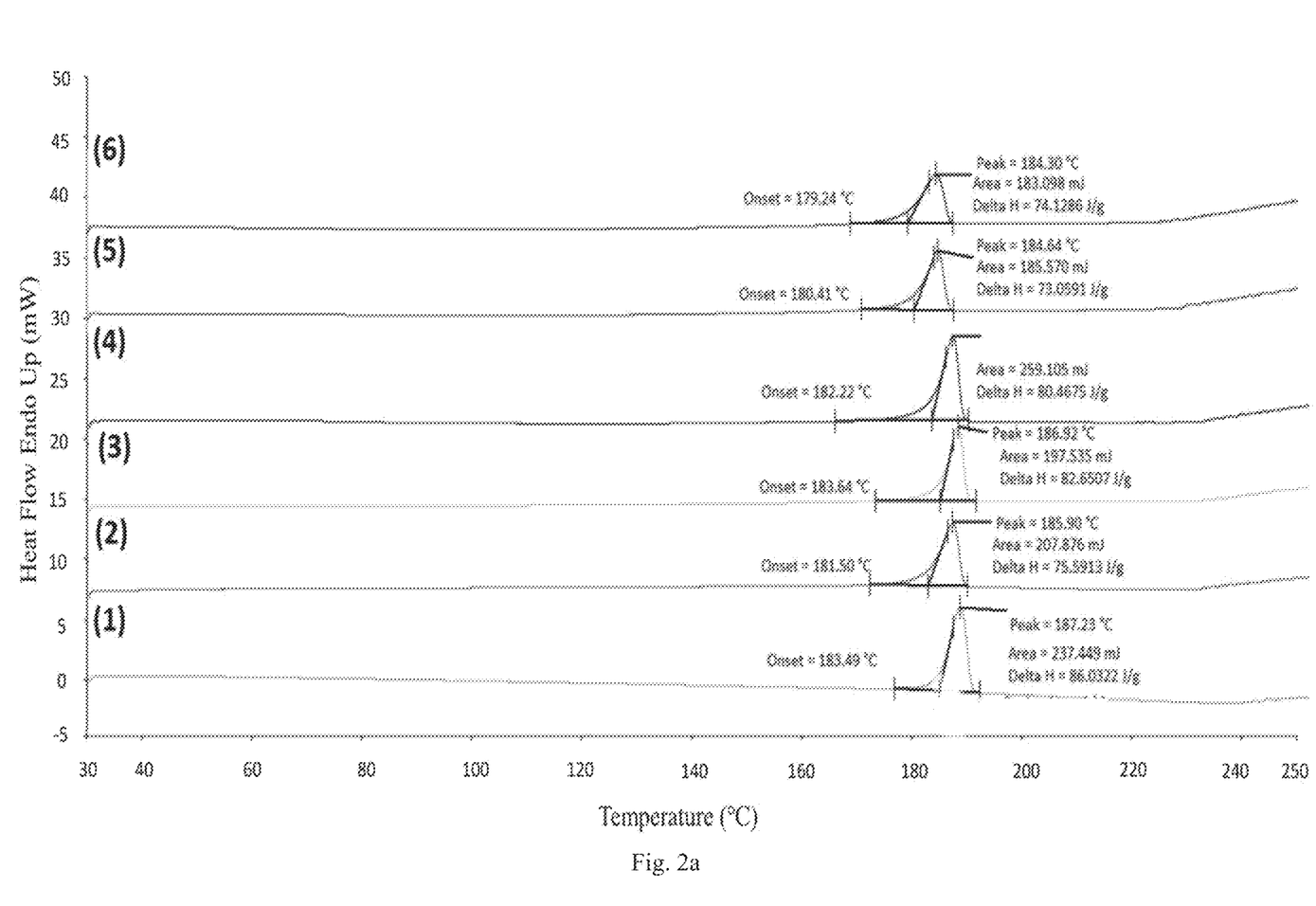
FIGS. 2a and 2b illustrate DSC thermograms for the obtained crystalline forms of ABT-101 free base.
Figure 2B:
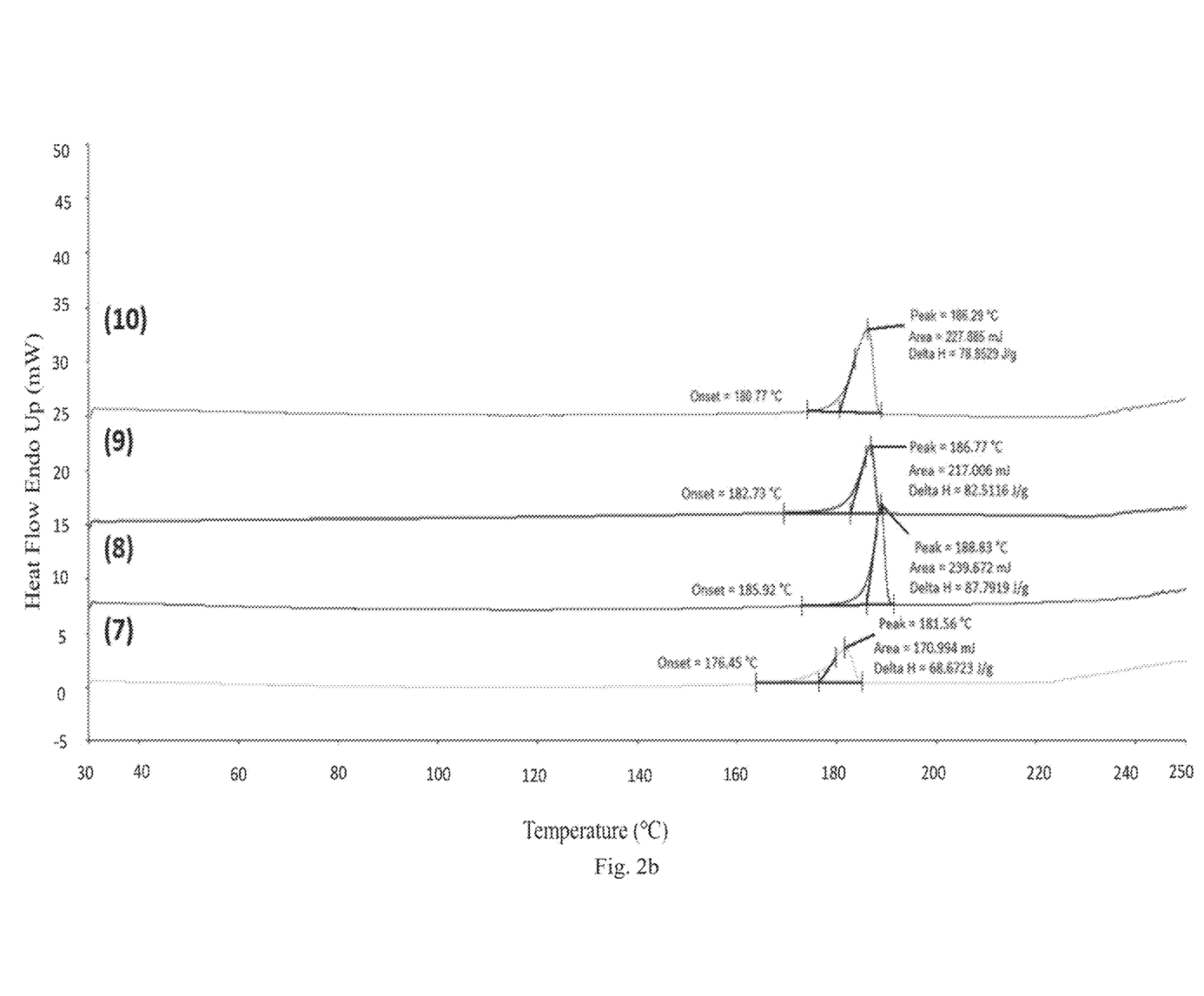
Figure 3:
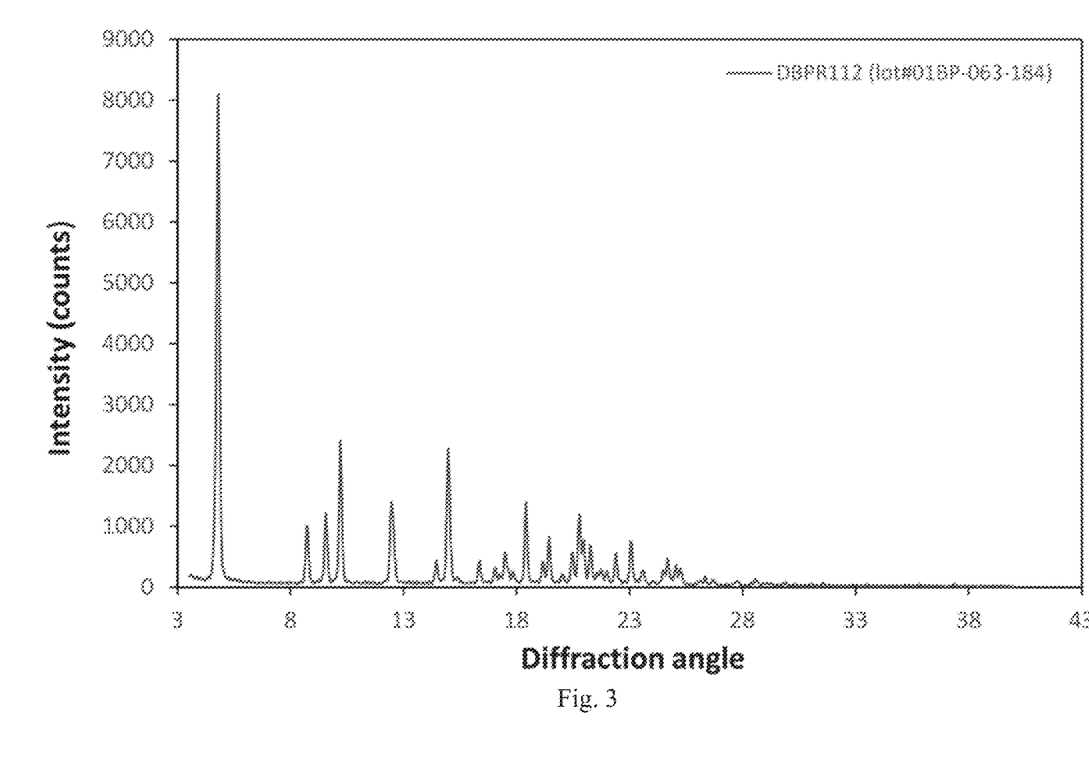
FIG. 3 illustrates a XRPD pattern for a crystalline form of ABT-101 free base (01BP-063-184)

The crystalline forms of ABT-101 free base are currently obtained and they are further tested for physical characterization. First of all, the DSC thermograms for the Page 1S of 25 samples of crystalline forms of ABT-101 free base made using different solvents are shown in FIGS. 2a and 2b. Secondly, a XRPD pattern for one of the crystalline forms of ABT-101 free base (01BP-063-184) is shown in FIG. 3, with corresponding tabulated data shown in Table 2.

TABLE 2

| Angle, 2-Theta deg. | d value, Angstrom | Intensity, CPS | Rel. Intensity, % | FWHM | Net Area |
|---|---|---|---|---|---|
| 4.8001 | 18.3947 | 7900 | 100.0 | 0.1541 | 8.8055 |
| 8.7378 | 10.1118 | 928 | 11.8 | 0.1456 | 0.9095 |
| 9.5665 | 9.2377 | 1126 | 14.2 | 0.1450 | 1.0453 |
| 10.2104 | 8.6566 | 2308 | 29.2 | 0.1381 | 2.1490 |
| 12.4840 | 7.0847 | 1254 | 15.9 | 0.2025 | 1.7084 |
| 14.4496 | 6.1250 | 357 | 4.5 | 0.1295 | 0.2668 |
| 14.9758 | 5.9110 | 216.3 | 27.4 | 0.1579 | 2.2215 |
| 16.3570 | 5.4148 | 358 | 4.5 | 0.1308 | 0.3151 |
| 17.0475 | 5.1970 | 230 | 2.9 | 0.1291 | 0.1506 |
| 17.5005 | 5.0635 | 476 | 6.0 | 0.1382 | 0.3789 |
| 17.8549 | 4.9638 | 182 | 2.3 | 0.1094 | 0.1048 |
| 18.4159 | 4.8138 | 1291 | 16.3 | 0.1327 | 1.1317 |
| 19.1670 | 4.6269 | 343 | 4.3 | 0.1237 | 0.2171 |
| 19.4424 | 4.5619 | 733 | 9.3 | 0.1270 | 0.5287 |
| 20.0442 | 4.4263 | 109 | 1.4 | 0.1296 | 0.0937 |
| 20.4684 | 4.3355 | 468 | 5.9 | 0.1359 | 0.3353 |
| 20.7804 | 4.2711 | 1085 | 13.7 | 0.1249 | 0.5076 |
| 20.9560 | 4.2357 | 648 | 8.2 | 0.0834 | 0.2240 |
| 21.2721 | 4.1735 | 593 | 7.5 | 0.1216 | 0.4064 |
| 21.7373 | 4.0852 | 187 | 2.4 | 0.1018 | 0.0922 |
| 21.9986 | 4.0373 | 166 | 2.1 | 0.1169 | 0.1122 |
| 22.3964 | 3.9665 | 450 | 5.7 | 0.1257 | 0.3548 |
| 23.0598 | 3.8538 | 673 | 8.5 | 0.1442 | 0.6124 |
| 23.5839 | 3.7694 | 200 | 2.5 | 0.1685 | 0.1863 |
| 24.5116 | 3.6288 | 212 | 2.7 | 0.1200 | 0.0531 |
| 24.6908 | 3.6028 | 411 | 5.2 | 0.1065 | 0.1890 |
| 25.0497 | 3.5520 | 298 | 3.8 | 0.1194 | 0.1421 |
| 25.2468 | 3.5247 | 244 | 3.1 | 0.1134 | 0.0927 |
| 26.0950 | 3.4120 | 60 | 0.8 | 0.1427 | 0.0336 |
| 26.3527 | 3.3793 | 130 | 1.6 | 0.0826 | 0.0656 |
| 26.6922 | 3.3371 | 81 | 1.0 | 0.1145 | 0.0581 |

Figure 4:
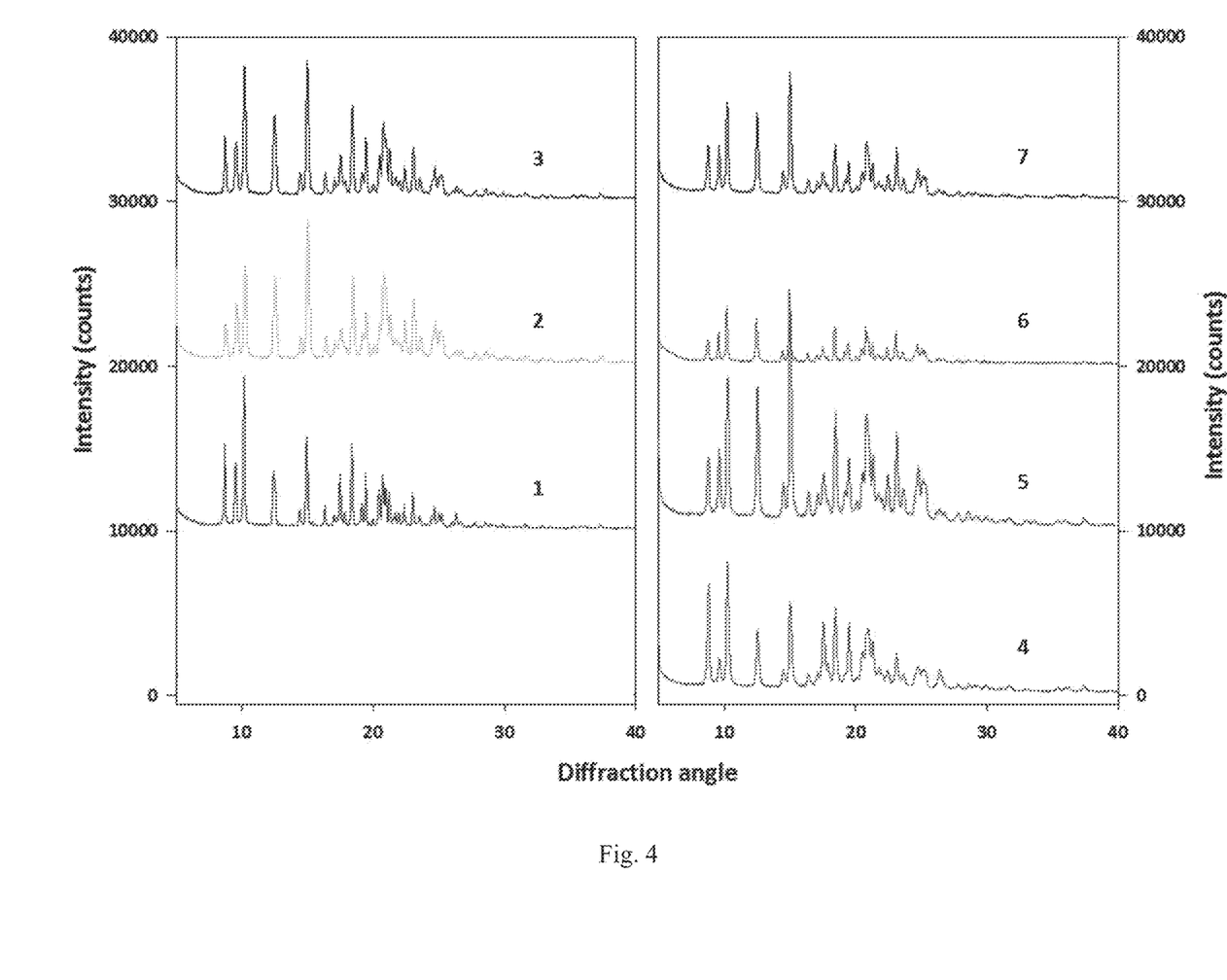
FIG. 4 illustrates XRPD patterns for crystalline forms of ABT-101 free base.

Besides, XRPD patterns for crystalline forms of ABT-101 free base made using different solvents are aligned and compared in FIG. 4.

Example 3

Comparison of Different Solid Crystal Forms of ABT-101

In this section, different solid crystal forms of ABT-101 are compared as shown in Table 3.

TABLE 3

| Solid Form | | Free Base | Glycollate | Succinate | Hydrochloride |
|---|---|---|---|---|---|
| Crystallinity (XRPD) | | Crystalline | Crystalline | Crystalline | Crystalline |
| Melting Point (° C.) (DSC) | | 184.2 | 163.5 | 146.7 | 216.2 |
| Enthalpy of melting (J/g) (DSC) | | 81.1 | 88.9 | 60.5 | 64.6 |
| Weight loss before melting (%) (TGA) | | 0.6 wt % | 0.7 wt % | 0.5 wt % | 3.6 wt % |
| Hygroscopicity (%) (DVS) (Water uptake at 80% RH at 25° C.) | | 0.96 | 0.49 | 1.88 | 7.65 |
| Crystal form change post DVS | | No change | No change | Amorphous | No change |
| Solubility 24 hrs | FaSSIF | 0.32 | 1.1 | >9.4 | 0.90 |
| | FeSSIF | 0.41 | >11.3 | >9.4 | 0.29 |
| | SGF | 9.1 | >10.9 | >9.9 | 5.2 |
| | H$_2$O | 0.02 | >10.5 | >10.1 | 10.5 |
| Stability | 80° C., 24 hrs | Stable | Stable | Stable | Stable |
| | 25° C./60% RH, 1 week | Stable | Stable | Stable | Stable |
| | 40° C./75% RH, 1 week | Stable | Unstable | Unstable | Stable |

In Table 3, "FaSSIF" stands for "Fasted state simulated intestinal fluid"; "FeSSIF" stands for "Fed state simulated intestinal fluid"; "SGF" stands for "Simulated gastric fluid".

According to Table 3, it can be inferred that the free base form of ABT-101, compared with the glycollate form, succinate form and hydrochloride form, exhibits improved "weight loss before melting", "hygroscopicity", "crystal form change post DVS", "solubility", and "stability".

Figure 5:
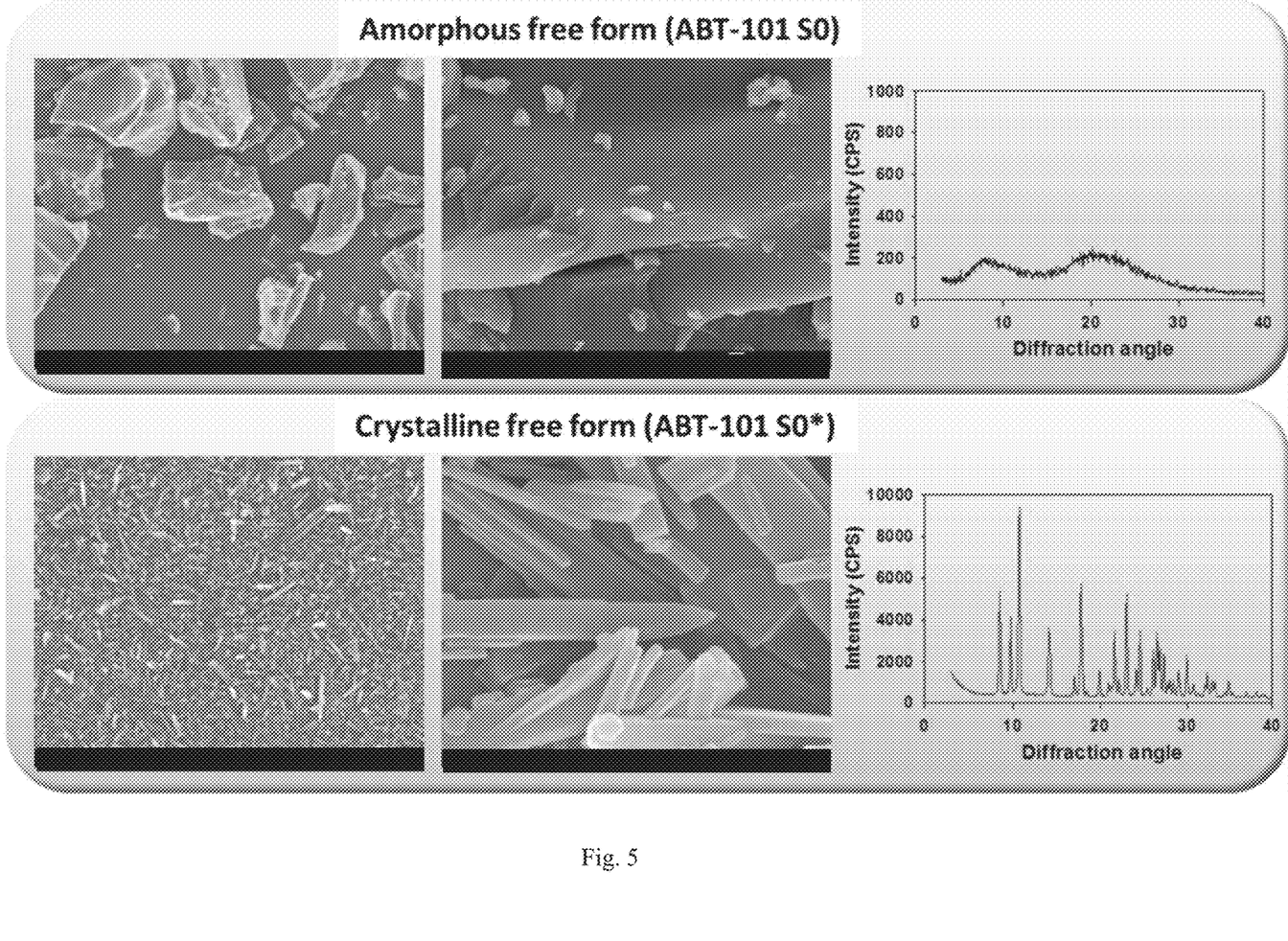
FIG. 5 illustrates the comparison of amorphous free form (00BP-081-154) and crystalline free form (01BP-063-120) of ABT-101.

Besides, the comparison between of amorphous free form ABT-101S0) and crystalline free form (ABT-101S0*) of ABT-101 is shown in FIG. 5.

Example 4

Pharmacokinetics Study

In this section, the pharmacokinetics of the crystal form (ABT-101S0*) and amorphous form (ABT-101S0) of ABT-101 are examined and compared, and the result thereof is shown in Table 4.

TABLE 4

| Compound | Rat IV | | | | | Rat PO | | | | | |
|---|---|---|---|---|---|---|---|---|---|---|---|
| | Dose (mg/kg) | $T_{1/2}$ (hr) | CL (ml/min/kg) | $V_{ss}$ (l/kg) | $AUC_{(0-inf)}$ (ng/mL * hr) | Dose (mg/kg) | $C_{max}$ (ng/ml) | $T_{max}$ (hr) | $T_{1/2}$ (hr) | $AUC_{(0-inf)}$ (ng/mL * hr) | F (%) |
| ABT-101 S0 | 5 | 2.3 | 55.6 | 8.6 | 1520 | 20 | 136 | 4 | 4.7 | 1179 | 19 |
| ABT-101 S0* | 5 | 2.3 | 55.6 | 8.6 | 1520 | 20 | 508 | 3.3 | 3.4 | 2978 | 42 |

According to Table 4, the crystal form (ABT-101 S0*) of ABT-101 having increased Cmax, AUC and F (%) about 1.9~3 times compared to amorphous form (ABT-101 S0).

Example 5

Stability Study

In this section, the stability of the crystalline form of ABT-101 free base as active pharmaceutical ingredients (API) is tested from various aspects.

First of all, the long term stability of the crystalline form of ABT-101 free base as tested is shown in Table 5.

TABLE 5

Long term stability of ABT-101 free base

| | Conditions 25° C., 60% RH | | |
|---|---|---|---|
| Time | Solid Form | Purity | Physical Property |
| 1 week | Free Base | Stable | No Change detected |
| 3 months | Free Base | Stable | No Change detected |
| 6 months | Free Base | Stable | No Change detected |
| 12 months | Free Base | Stable | No Change detected |
| 24 months | Free Base | Stable | No Change detected |
| 36 months | Free Base | Stable | No Change detected |
| 60 months | Free Base | Stable | No Change detected |

Secondly, a pharmaceutical composition, more particularly, a capsule comprising different content (25 mg and 100 mg respectively) of the crystalline form of ABT-101 free base as API (ABT-101 free base) is currently made, and the compositions thereof are shown in Table 6.

TABLE 6

Compositions of capsule of two strengths

| Component | Component Role | 25 mg capsule (mg/ea) | 100 mg capsule (mg/ea.) |
|---|---|---|---|
| ABT-101 free base | Active ingredient | 25.0 | 100.0 |
| pharmaceutically acceptable carrier or excipient | | 95.0 | 380.0 |
| Total Weight (mg) | | 120.0 | 480.0 |

Further, the ABT-101 capsules described above are tested following the program shown in Table 7; wherein: "S" stands for stability test; "M" stands for microbial limit test (MVLT); "(-)" stands for optional, sample only pulled and tested when needed.

TABLE 7

| Storage Condition | Sampling Frequency (Months) | | | | | | | |
|---|---|---|---|---|---|---|---|---|
| | 0 | 1 | 3 | 6 | 9 | 12 | 18 | 24 | 36 |
| 25° C., 60% RH | S + M | S | S | S + M | S | S + M | S | S + M | S + M |
| 30° C., 65% RH | | (S) | (S) | (S) | (S) | (S) | — | — |
| 40° C., 75% RH | | S | S | S + M | — | — | — | — |

Accordingly, the stability data of the 25 mg capsule and 100 mg capsule described above under long-term storage condition (25° C., 60% RH) are shown in Table 8 and Table 9 respectively; and the comparison between them is shown in Table 10.

TABLE 8

| Parameter | Acceptance Criteria | Months | | | | |
|---|---|---|---|---|---|---|
| | | 0 | 1 | 3 | 6 | 9 |
| Appearance | Size 4, Capsules with powder, white opaque cap/white opaque body | Complies | Complies | Complies | Complies | Complies |
| Identification | The retention time of main peak in sample solutions corresponds to that of the Standard solution, as obtained in the Assay | Conforms | Conforms | Conforms | Conforms | Conforms |

TABLE 8-continued

| | | | | | | |
|---|---|---|---|---|---|---|
| Assay | % Label Claim: 90.0%-110.0% | 98.9% | 98.4% | 99.6% | 97.5% | 98.9% |
| Related substance | Any individual impurity: NMT 0.5%<br>Total impurities: NMT 2.0% | RRT 0.91: <0.05%<br>RRT 1.18: 0.06%<br>RRT 1.43-1.44: 0.06%<br>RRT 1.67: 0.06%<br>Total: 0.19% | RRT 0.92: <0.05%<br>RRT 1.19: 0.06%<br>RRT 1.44: 0.07%<br>RRT 1.67-1.68: 0.05%<br>Total: 0.19% | RRT 1.19: 0.07%<br>RRT 1.39: 0.10%<br>RRT 1.57: <0.05%<br>RRT 1.64: 0.06%<br>Total: 0.23% | RRT 1.37: 0.13%<br>RRT 1.71: <0.05%<br>RRT 1.83: 0.05%<br>Total: 0.18% | RRT 0.91: <0.05%<br>RRT 1.32: <0.05%<br>RRT 1.54: 0.13%<br>RRT 1.73: 0.09%<br>Total: 0.27% |
| Water content | Report results | 3.2% | 2.8% | 3.1% | 4.0% | 3.1% |
| Dissolution | Q ≥ 80% at 15 minutes | 99.0% | 98.1% | 98.5% | 100.9% | 102.1% |

| | | Months | | | |
|---|---|---|---|---|---|
| Parameter | Acceptance Criteria | 12 | 18 | 24 | 36 |
| Appearance | Size 4, Capsules with powder, white opaque cap/white opaque body | Complies | Complies | Complies | Complies |
| Identification | The retention time of main peak in sample solutions corresponds to that of the Standard solution, as obtained in the Assay | Conforms | Conforms | Conforms | Conforms |
| Assay | % Label Claim: 90.0%-110.0% | 98.9% | 98.4% | 98.3% | 99.3% |
| Related substance | Any individual impurity: NMT 0.5%<br>Total impurities: NMT 2.0% | RRT 0.91: <0.05%<br>RRT 1.12: <0.05%<br>RRT 1.21: <0.05%<br>RRT 1.46: 0.17%<br>RRT 2.03: <0.05%<br>RRT 2.24: 0.06%<br>Total: 0.23% | RRT 1.48: 0.21%<br>RRT 2.28: 0.06%<br>Total: 0.27% | RRT 1.46: 0.22%<br>RRT 2.70: 0.06%<br>Total: 0.27% | RRT 0.92: 0.05%<br>RRT 1.19: <0.05%<br>RRT 1.30: 0.06%<br>RRT 1.47: 0.30%<br>RRT 1.61: 0.12%<br>RRT 2.06: 0.10%<br>Total: 0.62% |
| Water content | Report results | 3.0% | 3.3% | 3.0% | 3.3% |
| Dissolution | Q ≥ 80% at 15 minutes | 105.2% | 102.5% | 103.2% | 100.4% |

TABLE 9

| | | Months | | | | | |
|---|---|---|---|---|---|---|---|
| Parameter | Acceptance Criteria | 0 | 1 | 3 | 6 | 9 | 12 |
| Appearance | Size 0, Capsules with powder, scarlet opaque cap/scarlet opaque body | Complies | Complies | Complies | Complies | Complies | Complies |
| Identification | The retention time of main peak in sample solutions corresponds to that of the Standard solution, as obtained in the Assay | Conforms | Conforms | Conforms | Conforms | Conforms | Conforms |
| Assay | % Label Claim: 90.0%-110.0% | 99.5% | 98.3% | 99.7% | 98.6% | 100.1% | 100.1% |
| Related substance | Any individual impurity: NMT 0.5%<br>Total impurities: NMT 2.0% | RRT 0.92: <0.05%<br>RRT 1.18: 0.07%<br>RRT 1.44: 0.06%<br>RRT 1.62: <0.05%<br>RRT 1.68: 0.06%<br>Total: 0.19% | RRT 0.92: 0.05%<br>RRT 1.19: 0.06%<br>RRT 1.44: 0.08%<br>RRT 1.68: 0.06%<br>Total: 0.25% | RRT 1.19: 0.07%<br>RRT 1.39: 0.11%<br>RRT 1.57: <0.05%<br>RRT 1.64: 0.06%<br>Total: 0.24% | RRT 1.37: 0.15%<br>RRT 1.71: <0.05%<br>RRT 1.83: 0.05%<br>Total: 0.21% | RRT 0.91: <0.05%<br>RRT 1.32: <0.05%<br>RRT 1.55: 0.16%<br>RRT 1.73: 0.09%<br>Total: 0.25% | RRT 0.91: <0.05%<br>RRT 1.12: <0.05%<br>RRT 1.21: <0.05%<br>RRT 1.47: 0.21%<br>RRT 2.02: <0.05%<br>RRT 2.24: 0.06%<br>Total: 0.27% |
| Water content | Report results | 3.4% | 3.3% | 3.6% | 3.7% | 3.5% | 3.5% |
| Dissolution | Q ≥ 80% at 15 minutes | 100.4% | 100.9% | 98.3% | 101.0% | 100.8% | 99.7% |

TABLE 9-continued

| Parameter | Acceptance Criteria | Months | | | | |
|---|---|---|---|---|---|---|
| | | 18 | 21 | 24 | 28 | 36 |
| Appearance | Size 0, Capsules with powder, scarlet opaque cap/ scarlet opaque body | Complies | Complies | Complies | Complies | Complies |
| Identification | The retention time of main peak in sample solutions corresponds to that of the Standard solution. as obtained in the Assay | Conforms | Conforms | Conforms | Conforms | Conforms |
| Assay | % Label Claim: 90.0%-110.0% | 98.4% | 97.7% | 99.3% | 97.8% | 98.4% |
| Related substance | Any individual impurity: NMT 0.5% Total impurities: NMT 2.0% | RRT 1.48: 0.27% RRT 2.27: 0.06% Total: 0.33% | RRT 1.48: 0.27% RRT 2.26: 0.06% Total: 0.33% | RRT 1.46: 0.29% RRT 2.69: 0.06% Total: 0.35% | RRT 1.50: 0.32% RRT 2.35: 0.06% Total: 0.37% | RRT 0.92: 0.06% RRT 1.19: <0.05% RRT 1.29: 0.05% RRT 1.47: 0.38% RRT 1.60: 0.11% RRT 2.06: 0.11% Total: 0.71% |
| Water content | Report results | 3.7% | 3.4% | 3.5% | 3.7% | 3.7% |
| Dissolution | Q ≥ 80% at 15 minutes | 99.2% | 98.9% | 100.4% | 97.8% | 99.3% |

TABLE 10

Physical stability of Free Base capsule of two different strengths

| | Conditions 25° C., 60% RH | |
|---|---|---|
| Time | 25 mg capsule | 100 mg capsule |
| 1 week | No Change detected | No Change detected |
| 3 months | No Change detected | No Change detected |
| 6 months | No Change detected | No Change detected |
| 12 months | No Change detected | No Change detected |
| 24 months | No Change detected | No Change detected |
| 36 months | Individual impurity >0.5% | Individual impurity >0.5% |

In summary, the crystalline forms of ABT-101 free base can exhibit unexpected stability and improved pharmacokinetic properties compared to other forms or salt thereof, thereby allowing said compound more suitable for drug development and satisfying the requirements for bioavailability and drug efficacy. The specific embodiments of the present invention have been disclosed, but it is not intended to limit the present invention. Those with ordinary knowledge in the technical field to which the present invention belongs are capable of understanding. And in the case of deviating from the principle and spirit of the present invention, various changes and modifications can be made to it, so the scope of protection of the present invention should be based on those defined in the scope of the accompanying patent application.

What is claimed is:

1. A crystalline form of (S, E)-4-(dimethylamino)-N-(3-(4-(2-hydroxy-1-phenylethylamino)-6-phenylfuro[2,3-d]pyrimidin-5-yl)phenyl)but-2-enamide (ABT-101) free base having an X-ray powder diffraction pattern comprising peaks at 2θvalues of 4.8°±0.2°, 9.5°±0.2°, 10.2°±0.2°, 12.5°±0.2°, 15.0°±0.2°, 18.4°±0.2° and 20.8°±0.2°.

2. The crystalline form of claim 1, having an X-ray powder diffraction pattern further comprising a peak at 2θvalue of 8.7°±0.2°.

3. The crystalline form of claim 1, having an X-ray powder diffraction pattern further comprising a peak at 2θvalue of 19.4°±0.2°.

4. The crystalline form of claim 1, having an X-ray powder diffraction pattern further comprising a peak at 2θvalue of 23.1°±0.2°.

5. The crystalline form of claim 1, having a melting point temperature of 170 to 195° C.

6. The crystalline form of claim 1, having an enthalpy of melting of 75 to 85 J/g.

7. A pharmaceutical composition comprising the crystalline form of claim 1, and a pharmaceutically acceptable carrier or excipient.

8. The pharmaceutical composition of claim 7, which is an EGFR inhibitor, a HER2 inhibitor or a tumor-agnostic inhibitor.

9. The pharmaceutical composition of claim 7, which is in a form of a capsule.

10. The pharmaceutical composition of claim 9, comprising from 0.1 to 200 mg of the crystalline form.

11. The pharmaceutical composition of claim 9, comprising from 25 to 100 mg of the crystalline form.

12. The pharmaceutical composition of claim 9, comprising from 50 to 100 mg of the crystalline form.

13. The pharmaceutical composition of claim 9, wherein the pharmaceutically acceptable carrier or excipient comprises a filler.

14. The pharmaceutical composition of claim 9, wherein the pharmaceutically acceptable carrier or excipient comprises a disintegrant.

15. The pharmaceutical composition of claim 9, wherein the pharmaceutically acceptable carrier or excipient comprises a lubricant.

16. A method of treating cancer, comprising administering to a patient in need thereof a therapeutically effective amount of the crystalline form of claim 1.

17. The method of claim 16, wherein the crystalline form is an EGFR inhibitor, a HER2 inhibitor or a tumor-agnostic inhibitor.

18. The method of claim 16, wherein the cancer is peritoneal cancer, small intestine cancer, non-small cell lung cancer (NSCLC), neuroendocrine cancer, salivary gland, bladder cancer, breast cancer, cervix cancer, bile duct cancer, esophageal cancer, stomach cancer, early gastric cancer, colorectal cancer, prostate cancer, ovarian cancer, head and neck cancer, endometrial cancer, kidney cancer, melanoma cancer, sarcoma cancer, pancreatic cancer, small cell lung cancer (SCLC), leukemia cancer, brain cancer or thyroid cancer.

* * * * *